US012593979B2

(12) United States Patent
Welsher

(10) Patent No.:  US 12,593,979 B2
(45) Date of Patent:        Apr. 7, 2026

(54) WEARABLE VITAL SIGN MONITOR DEVICE

(71) Applicant: Wayne Welsher, Rogers, AR (US)

(72) Inventor:  Wayne Welsher, Rogers, AR (US)

( * ) Notice:    Subject to any disclaimer, the term of this patent is extended or adjusted under 35 U.S.C. 154(b) by 328 days.

(21) Appl. No.: 18/466,244

(22) Filed:    Sep. 13, 2023

(65)            Prior Publication Data

US 2024/0306912 A1      Sep. 19, 2024

Related U.S. Application Data

(60) Provisional application No. 63/452,190, filed on Mar. 15, 2023.

(51) Int. Cl.
   *A61B 5/00*          (2006.01)
   *A61B 5/0205*        (2006.01)
   *A61B 5/318*         (2021.01)
(52) U.S. Cl.
   CPC .......... *A61B 5/0015* (2013.01); *A61B 5/0205* (2013.01); *A61B 5/318* (2021.01); *A61B 5/681* (2013.01); *A61B 5/6885* (2013.01); *A61B 5/742* (2013.01); *A61B 2503/20* (2013.01)
(58) Field of Classification Search
   CPC ..... A61B 5/0015; A61B 5/0205; A61B 5/318; A61B 5/681; A61B 5/6885; A61B 5/742; A61B 5/6831
   See application file for complete search history.

(56)                References Cited

U.S. PATENT DOCUMENTS 10,582,868 B1 *   3/2020  Ahmad .................. A61B 5/339
2007/0265533 A1 * 11/2007  Tran ..................... A61B 5/0006
                                                600/528
2017/0127958 A1 *   5/2017  Ungureanu ............ A61B 5/746
2017/0251935 A1 *   9/2017  Yuen .................. A61B 5/02116
2021/0321953 A1 *  10/2021  Panneer Selvam .... A61B 5/681
2023/0095971 A1 *   3/2023  He ......................... A61B 5/282
                                                600/301

* cited by examiner

*Primary Examiner* — Paula J Stice
(74) *Attorney, Agent, or Firm* — Brennan, Manna & Diamond, LLC

(57)                ABSTRACT

A vital sign monitoring device is disclosed that measures the pulse, blood pressure, tissue oximetry, respiratory rate, and EKG lead of a suspect in police custody and/or a police officer. The device is comprised of a base component comprising a blood pressure monitor, a pulse monitor, an oximeter, an EKG lead, and a respiration monitor. The base component is then inserted into a wristband component, such that a user can wear the device on their wrists. The device records vital signs of the user and triggers alarms when vital signs exceed the specific parameters. Further, the device comprises a touchscreen that graphically displays vital signs being monitored.

4 Claims, 12 Drawing Sheets

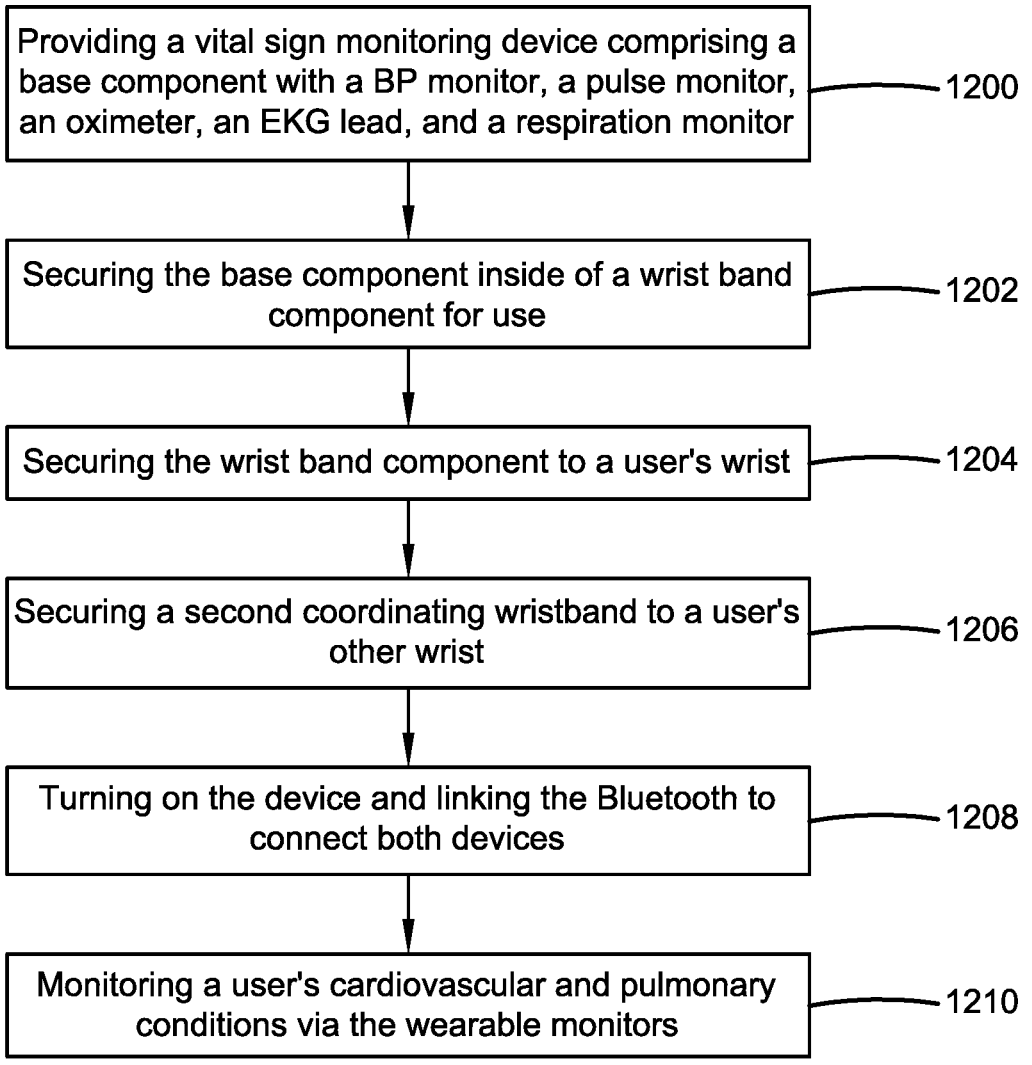

Providing a vital sign monitoring device comprising a base component with a BP monitor, a pulse monitor, an oximeter, an EKG lead, and a respiration monitor 〜1200

Securing the base component inside of a wrist band component for use 〜1202

Securing the wrist band component to a user's wrist 〜1204

Securing a second coordinating wristband to a user's other wrist 〜1206

Turning on the device and linking the Bluetooth to connect both devices 〜1208

Monitoring a user's cardiovascular and pulmonary conditions via the wearable monitors 〜1210

FIG. 12

WEARABLE VITAL SIGN MONITOR DEVICE

CROSS-REFERENCE TO RELATED APPLICATION

The present application claims priority to, and the benefit of, U.S. Provisional Application No. 63/452,190, which was filed on Mar. 15, 2023, and is incorporated herein by reference in its entirety.

FIELD OF THE INVENTION

The present invention relates generally to the field of vital sign monitoring devices. More specifically, the present invention relates to a vital sign monitoring device that monitors vital signs of a user, such as pulse, blood pressure, tissue oximetry, respiratory rate, and EKG lead. Accordingly, the present disclosure makes specific reference thereto. Nonetheless, it is to be appreciated that aspects of the present invention are also equally applicable to other like applications, devices, and methods of manufacture.

BACKGROUND

By way of background, this invention relates to improvements in vital sign monitoring devices. Generally, there is a broad need for monitoring multiple physiologic parameters in individuals under extreme stress. Whether in military, athletics, or law enforcement, life threatening situations may easily be missed without sophisticated measurement of specific cardiovascular and pulmonary conditions. As an example, police suspects may be unpredictable while in custody. Furthermore, police officers may not be able to recognize the rapidly deteriorating condition of a suspect in time to safely navigate the changing circumstances. As a result, a suspect may suffer a medical emergency and/or death.

Known vital sign monitors worn on the wrist are extremely limited in functionality. For example, some conventional monitors simply monitor and display pulse rate and thus provide no EKG data recording capability at all, as well as other pulmonary or cardiovascular conditions. Other monitors record data and provide only for the local playback of recorded data and thus, provide no remote diagnostic capability. Still others require external electrodes or other monitoring components that are difficult to hook up and use, especially for long-term monitoring of a relatively active patient. Subsequently, problems abound in producing small, lightweight cardiovascular and pulmonary monitors that provide for long-term monitoring and recording.

Accordingly, it is a principal object of the present invention to provide a self-contained, vital sign monitor, worn on the wrist, that provides event recording and telecommunication of vital sign data to a remote site for professional diagnosis. Further, a need exists for a vital sign monitoring device that monitors the pulse, blood pressure, tissue oximetry, respiratory rate, and EKG lead of a user.

Therefore, there exists a long-felt need in the art for a vital sign monitoring device that provides users with a device that can be worn on a user's wrist. There is also a long-felt need in the art for a vital sign monitoring device that provides a wearable device that monitors vital signs of a suspect in police custody. Further, there is a long-felt need in the art for a vital sign monitoring device that monitors a user's pulse, blood pressure, tissue oximetry, respiratory rate, and EKG lead. Moreover, there is a long-felt need in the art for a device that sounds an alarm when vital signs exceed specific parameters. Further, there is a long-felt need in the art for a vital sign monitoring device that comprises a screen to graphically display a user's vital signs. Finally, there is a long-felt need in the art for a vital sign monitoring device that is inserted into a wristband for use.

The subject matter disclosed and claimed herein, in one embodiment thereof, comprises a vital sign monitoring device. The device is a wearable vital sign monitoring device that preferably measures the pulse, blood pressure, tissue oximetry, respiratory rate, and EKG lead of a suspect in police custody and/or a police officer. The device is comprised of a base component comprising a blood pressure monitor, a pulse monitor, an oximeter, an EKG lead, and a respiration monitor. The base component is then inserted into a wristband component, such that a user can wear the device on their wrists. The device records vital signs of the user and triggers alarms when vital signs exceed specific parameters. The device can be monitored remotely and data from the device can be recorded. Further, the device comprises a touchscreen that graphically displays vital signs being monitored. In one embodiment, a second base component is secured to a user's other wrist in a wristband component to ensure the correct parameters are measured. Additionally, the wristband comprises a tension warning component to prevent the band from being worn too tightly.

In this manner, the vital sign monitoring device of the present invention accomplishes all of the foregoing objectives and provides users with a device that provides a means of measuring a user's vital signs. The device is inserted into a wristband for use. The device can have an audible and/or visual alarm.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a vital sign monitoring device. The device is a wearable vital sign monitoring device that preferably measures the pulse, blood pressure, tissue oximetry, respiratory rate, and EKG lead of a suspect in police custody and/or a police officer. The device is comprised of a base component comprising a blood pressure monitor, a pulse monitor, an oximeter, an EKG lead, and a respiration monitor. The base component is then inserted into a wristband component, such that a user can wear the device on their wrists. The device records vital signs of the user and triggers alarms when vital signs exceed specific parameters.

In one embodiment, the vital sign monitoring device is an extremely compact and lightweight, full function cardiac and pulmonary monitor that conveniently and comfortably can be worn on the wrist of a user due to the form factor and size of the monitor's housing relative to the conventional wristband being only slightly larger than a traditional digital watch.

In one embodiment, the vital sign monitoring device is configured to be worn by a user on a wrist or forearm. Thus, a user can wear the vital sign monitoring device while performing activities. Such activities include both vigorous activities and sedentary activities. A few examples include running, bicycling, swimming, climbing, skiing, weightlifting, boxing, martial arts, gardening, desk work, resting, and sleeping.

In one embodiment, the vital sign monitoring device comprises a base component that can be any suitable shape and size as is known in the art, as long as the base component is not much bigger than a traditional watch or smartwatch so that it can be worn comfortably by a user. Further, the base component must be large enough to house a plurality of vital sign monitors and data generation means. Generally, the base component is rectangular in shape, but can be circular, square, oval, etc., or any other suitable shape as is known in the art. In some embodiments, the base component can be made of varying sizes, such that smaller sizes would be used for a woman and larger sizes used for a man.

In one embodiment, the base component is a touchscreen device that allows a user to enable and program the device via touching points on the screen. In another embodiment, the base component comprises functional buttons to enable a user to program and utilize the device. In yet another embodiment, the base component comprises both a touchscreen and functional buttons to enable a user to program the device.

In one embodiment, the base component comprises a plurality of vital sign monitors. Vital sign monitors include a blood pressure monitor, a pulse monitor, an oximeter, an EKG lead, a respiration monitor, etc., or any other suitable monitors as is known in the art. The plurality of vital sign monitors measure the pulse, blood pressure, tissue oximetry, respiratory rate, EKG lead of a user, etc., or any other suitable vital statistics as is known in the art. Further, the base component comprises electrodes, sensors, etc., and any other electronics needed to measure the plurality of vital signs.

In one embodiment, the base component comprises a plurality of electronics for measuring and monitoring vital signs, as well as recording data. The electronics can include, but are not limited to, an EKG signal amplifier, and hardware filters coupled with electrodes for producing an analog signal representative of the electrical field on the surface of a user's skin and between the electrodes. Electronics also include analog-to-digital signal conversion means (or analog-to-digital converter (ADC)), and an amplifier for producing digital data representing the user's EKG waveform over a predefined interval of time. Further, electronics preferably include static read-and-write memory (SRAM) that operate as a means for recording digital data produced by the ADC. Additional electronics include a microcontroller with read-only memory (ROM), a digital-to-analog converter (DAC), a voltage-controlled oscillator (VCO), and a speaker for wirelessly, and preferably audibly, communicating data recorded in the SRAM to a remote site for verification, real-time diagnosis, and/or archival recording.

In one embodiment, the vital sign monitoring device measures a user's blood pressure. In contrast to a traditional blood pressure cuff, blood pressure may instead, be measured by actuating an artery against a pressure sensor; for instance, by pushing the side of the index finger (where the radial artery resides) or the wrist against a force sensor whilst a photoplethysmogram or other blood flow pulse sensor measures the volume of blood passing through the artery. The user may be instructed on how much force to apply with his finger or wrist by providing visual or audio feedback with the readings from the force sensor. In this manner, signals corresponding to those of a traditional blood pressure cuff are captured, a varying and known force/pressure against an artery and a measure of the heartbeat signal (via i.e., EKG) to that force/pressure. The shape of the force sensor may be shaped in such a way as to accept the finger so that the relationship of force to pressure is well understood (i.e., linear). Further, a blood pulse amplitude sensor located on the back of the user's wrist may obtain blood pulse amplitude data from a capillary bed on the back of the user's wrist, while a blood pulse amplitude sensor located on the front of the user's wrist (palm side) may obtain blood pulse amplitude data from a radial artery on the user's wrist.

Systolic and/or diastolic blood pressure readings can be obtained by measuring variations in the amplitude of pulses in blood vessels, such as pulses in the volume of blood through arteries or capillary beds. Variations in blood pulse amplitude can be induced by applying varying external pressure against the blood vessels. In conventional oscillometric techniques for measuring blood pressure, an inflatable cuff applies the varying external pressure. In various embodiments of this disclosure, a user manually pushes against a location on his or her body and thereby applies the varying external pressure on the underlying blood vessels. While the user manually applies variable pressure, a sensor measures the blood pulse amplitude. A measuring device estimates the user's blood pressure from the pulse amplitude as a function of externally applied pressure.

In various embodiments, the blood pulse amplitude is determined using an optical sensor, such as a PPG sensor, which measures variations in blood volume through arteries. By measuring variations in amplitude of the PPG signal (and hence variations in blood volume amplitude pulses), as a function of variations in external pressure applied to the blood vessels used to generate PPG signal, sufficient information can be acquired to determine the systolic and/or diastolic blood pressure of a user.

In accordance with various embodiments, a user applies a variable pressure to his or her blood vessels while a PPG sensor measures the amplitude of blood volume pulses. The resulting PPG signal and associated pressure data is used to calculate blood pressure. Standard approaches to determining blood pressure from oscillometric data can be used.

In certain implementations, the blood pulse amplitude sensor is a photoplethysmogram (PPG) sensor, including a light emitter and a light detector, configured to generate PPG sensor data, but not limited to. Many other pressure sensitive techniques for measuring blood pulse amplitude may be used to estimate blood pressure in accordance with embodiments of this disclosure. In certain implementations, the blood pulse amplitude sensor is a bioelectrical impedance analysis (BIA) sensor or a ballistocardiograph (BCG) sensor.

In some embodiments, one or more processors are incorporated in the base component with the sensors. In certain embodiments, the vital sign monitoring device includes a wireless transmitter configured to transmit the blood pulse amplitude data and the variable force, and/or pressure data to a remote device. Further, at least one of the one or more processors may be located in the remote device. Specifically, the device additionally includes a wireless transmitter configured to transmit blood pulse amplitude data and variable force, and/or pressure data to a remote device. The transmitter may be attached to, or contained in, the base component. In certain embodiments, the one or more processors are located in the remote device. The remote device may be, for example, a smart phone, a tablet, a personal computer (i.e., a laptop computer), a server, a distributed computing environment, etc.

The one or more processors are typically integrated circuits, which may be general purpose integrated circuits or custom designed (or optimized) integrated circuits, such as digital signal processors. The processor(s) may operate under the control of program instructions including, for example, machine code and/or microcode stored on memory available to the processor(s) or embedded in the processor as, for example, firmware. As examples, the memory includes volatile memory such as random-access memory (DRAM or SRAM) or non-volatile memory, such as read only memory (ROM), EPROM, flash memory, and the like. Some or all of the memory may be disposed on the same integrated circuit that executes the instructions. Thus, in some embodiments, some or all of the memory may be considered to be included in the processor(s).

In certain embodiments, the vital sign monitoring device tracks the user's activity and uses activity type and/or activity level in determining whether to estimate blood pressure or how to estimate blood pressure. For example, the device may detect that a user just completed an exercise and based on that, the device may determine that is should not take a blood pressure reading or use a more stringent algorithm blood pressure estimation. This approach may be appropriate when the activity type or activity level is known to produce a blood pressure reading that would likely be inaccurate.

In one embodiment, the vital sign monitoring device comprises a means for recording data received from the monitoring of vital signs. This data can be graphically displayed to a user via the touchscreen of the base component. For example, users can read and record their measurements on the left side of the screen. If the user wishes to view a detailed readout of one of their measurements, the user merely touches the measurement on the left side of the screen. Once the measurement is selected by the user, the detailed analysis appears on the right side of the screen. Further, any other suitable user interface can be utilized to display the measurements, as is known in the art. Vital sign measurements are recorded as the device is used. Further, the data can be transferred remotely via a wireless connection. Thus, the data can be monitored and recorded remotely in real-time, as well. Base parameters for vital sign measurements can be established and set with the device, such that if a user's measurements are outside of the base parameters, an alarm is sounded. Specifically, if one of a user's measurements moves into a red zone (i.e., outside of the set base parameters), the right side of the screen will automatically display the dangerous measurement. At such a point, an alarm will begin to notify users of the situation. The alarm can be audible and/or visual. For example, the base component can comprise speakers to sound an alarm when a measurement enters the red zone. Further, the base component can comprise lights to flash an alarm when a measurement enters the red zone. In one embodiment, the base component comprises lights and speakers to sound and flash an alarm when a measurement enters the red zone.

In one embodiment, the vital sign monitoring device comprises a second device wherein the base component comprises the same size and shape as the previous base component and contains the same electronics and vital sign monitors. However, the second device does not comprise a touchscreen showing vital sign measurements but contains a hard plastic surface with at least two tactile buttons. The first button syncs its Bluetooth to the first base component.

Further, the second device also comprises an LED light next to the syncing button that illuminates green once the Bluetooth is synced. Any suitable number of buttons can be utilized as is known in the art.

In use, the two base components are each secured within a wristband component and worn on a user's wrist or forearm. Once synced and functioning, the device continuously measures pulse, blood pressure, tissue oximetry, respiratory rate, and an EKG lead. In one embodiment, only a single wristband device is used. If only one device is used, the respiratory rate and EKG cannot be monitored, but other vital signs can be measured. With the use of both devices, the pulse, blood pressure, tissue oximetry, respiratory rate, and an EKG lead can all be measured accurately.

In one embodiment, the wristband component is a conventional watchband of any suitable size and structure and, entirely contains the base component and electronics, sensors, etc. While the term wrist "band" is used herein, it is intended to cover all types of structure for fixing the base component to the user's wrist. The band may have a wide range of rigidities, so long as it can conform generally to the shape of the user's wrist. The concept of a wristband includes flexible wrist straps and bracelets with links. It also includes fixing structures that attach to watch faces and the like.

Further, the wristband component comprises a tension warning which alerts a user when the band is worn too tightly. Specifically, the wristband component comprises corrugated sides on the band. Warnings are printed within the folds of the corrugated sides, such that the warnings are not displayed when the band is not stretched. If the band becomes stretched, the corrugated sides expand and open, displaying the warnings to reduce tension on the band.

In one embodiment, the wristband component comprises a latch with inserts or prongs that fit into two to four holes, depending on the wants and/or needs of a user. Further, the wristband component comprises a flap or frame segment that lifts up and away from the band to allow the base component to be inserted into the screen face opening of the band. Once positioned in the band, the flap is secured back down to secure the base component within the band. The flap can have a notch, a tab, a lock, a pressure-fit, etc., to secure the flap in place once the base component has been inserted.

In one embodiment, the device comprises a speaker, lights, a micro-USB port, etc., or any other suitable components as is known in the art.

In one embodiment, the device is water resistant/waterproof or manufactured with a coating that is water resistant/waterproof.

Those skilled in the arts will appreciate that the illustrated and described base component, particularly of the electrodes, sensors, and electronics, achieve the extremely high functionality described herein, however, it is possible that alternative device selection and circuit topology, electronics, sensors, and/or electrodes might be used within the spirit of the invention. Those of skill also will appreciate that in accordance with the preferred embodiment, the base component and/or wristband component are molded plastic, such as acrylonitrile-butadiene-styrene (ABS), which renders the device extremely rigid and durable, but also lightweight and relatively inexpensive to manufacture.

In yet another embodiment, the vital sign monitoring device comprises a plurality of indicia.

In yet another embodiment, a method of monitoring a user's cardiovascular and pulmonary conditions via a wearable monitor is disclosed. The method includes the steps of providing a vital sign monitoring device comprising a base component with a blood pressure monitor, a pulse monitor, an oximeter, an EKG lead, and a respiration monitor. The method also comprises securing the base component inside a wristband component for use. Further, the method comprises securing the wristband component to a user's wrist. The method also comprises securing a second coordinating wristband component to a user's other wrist. The method comprises turning on the device and linking the Bluetooth to connect both devices. Finally, the method comprises monitoring a user's cardiovascular and pulmonary conditions via the wearable monitors.

Numerous benefits and advantages of this invention will become apparent to those skilled in the art to which it pertains, upon reading and understanding the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which:

FIG. 12 illustrates a flowchart showing the method of monitoring a user's cardiovascular and pulmonary conditions via a wearable monitor in accordance with the disclosed architecture.

DETAILED DESCRIPTION OF THE PRESENT INVENTION

Figure 1:
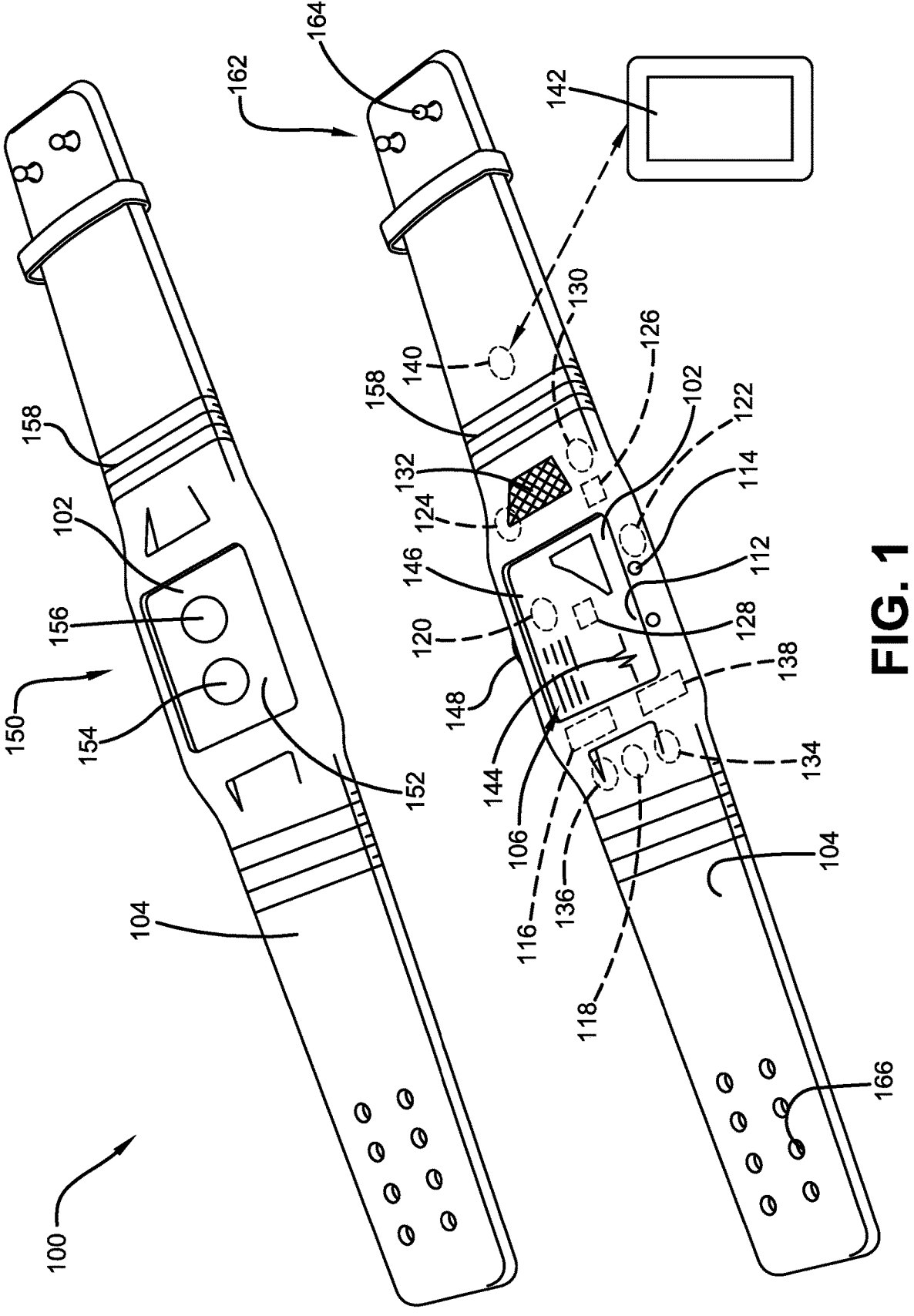
FIG. 1 illustrates a top perspective view of one embodiment of the vital sign monitoring device of the present invention showing the two wrist monitors in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for a vital sign monitoring device that provides users with a vital sign monitoring device that can be worn on a user's wrist. There is also a long-felt need in the art for a vital sign monitoring device that provides a wearable vital sign monitoring device that monitors vital signs of a suspect in police custody. Further, there is a long-felt need in the art for a vital sign monitoring device that monitors a user's pulse, blood pressure, tissue oximetry, respiratory rate, and EKG lead. Moreover, there is a long-felt need in the art for a device that sounds an alarm when vital signs exceed specific parameters. Further, there is a long-felt need in the art for a vital sign monitoring device that comprises a screen to graphically display a user's vital signs. Finally, there is a long-felt need in the art for a vital sign monitoring device that is inserted into a wristband for use.

The present invention, in one exemplary embodiment, is a novel vital sign monitoring device. The device is a wearable vital sign monitoring device that preferably measures the pulse, blood pressure, tissue oximetry, respiratory rate, and EKG lead of a suspect in police custody and/or a police officer. The device is comprised of a base component comprising a blood pressure monitor, a pulse monitor, an oximeter, an EKG lead, and a respiration monitor. The base component is then inserted into a wristband component, such that a user can wear the device on their wrists. The device records vital signs of the user and triggers alarms when vital signs exceed specific parameters. The present invention also includes a novel method of monitoring a user's cardiovascular and pulmonary conditions via a wearable monitor. The method includes the steps of providing a vital sign monitoring device comprising a base component with a blood pressure monitor, a pulse monitor, an oximeter, an EKG lead, and a respiration monitor. The method also comprises securing the base component inside a wristband component for use. Further, the method comprises securing the wristband component to a user's wrist. The method also comprises securing a second coordinating wristband component to a user's other wrist. The method comprises turning on the device and linking the Bluetooth to connect both devices. Finally, the method comprises monitoring a user's cardiovascular and pulmonary conditions via the wearable monitors.

Figure 2:
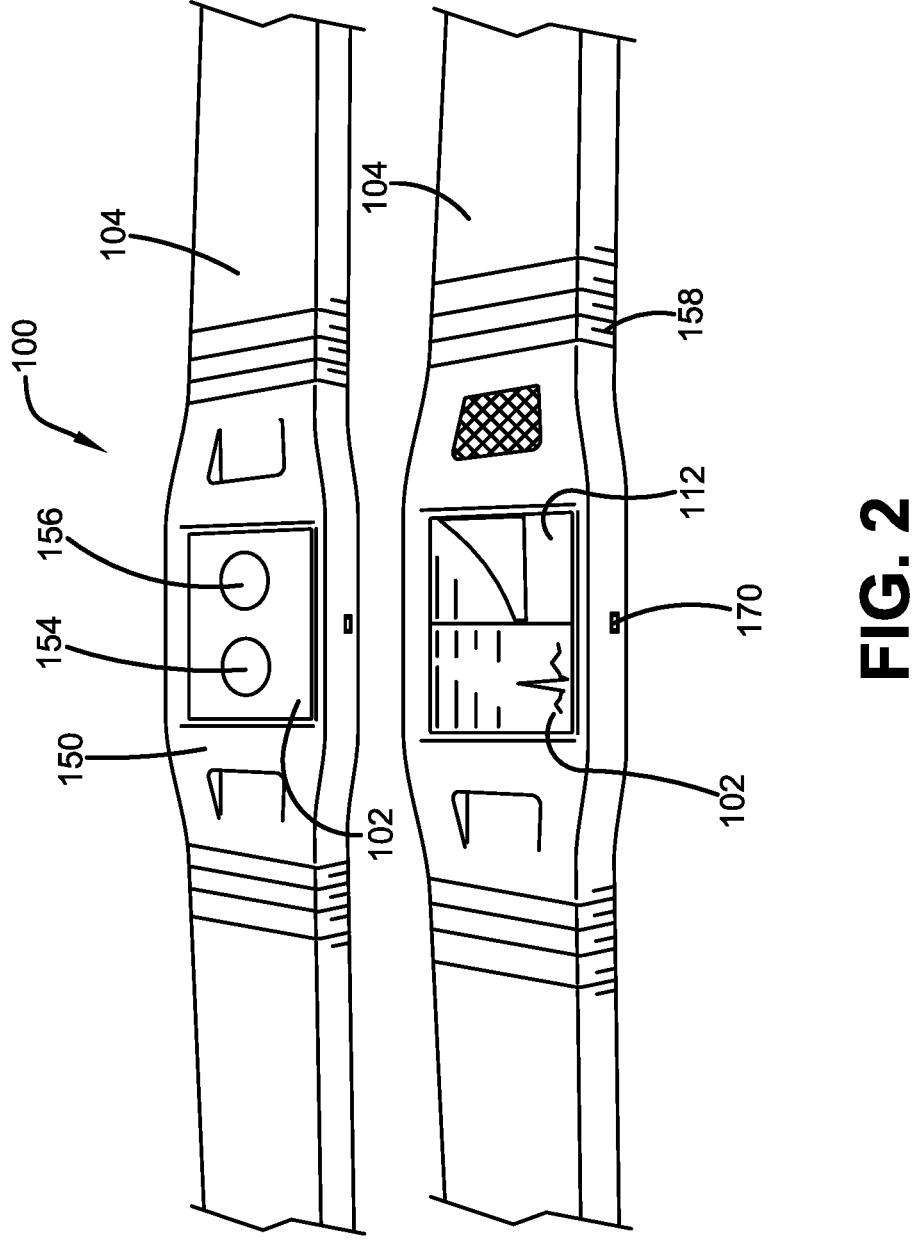
FIG. 2 illustrates a front perspective view of one embodiment of the vital sign monitoring device of the present invention showing the touchscreens in accordance with the disclosed architecture.
Figure 3:
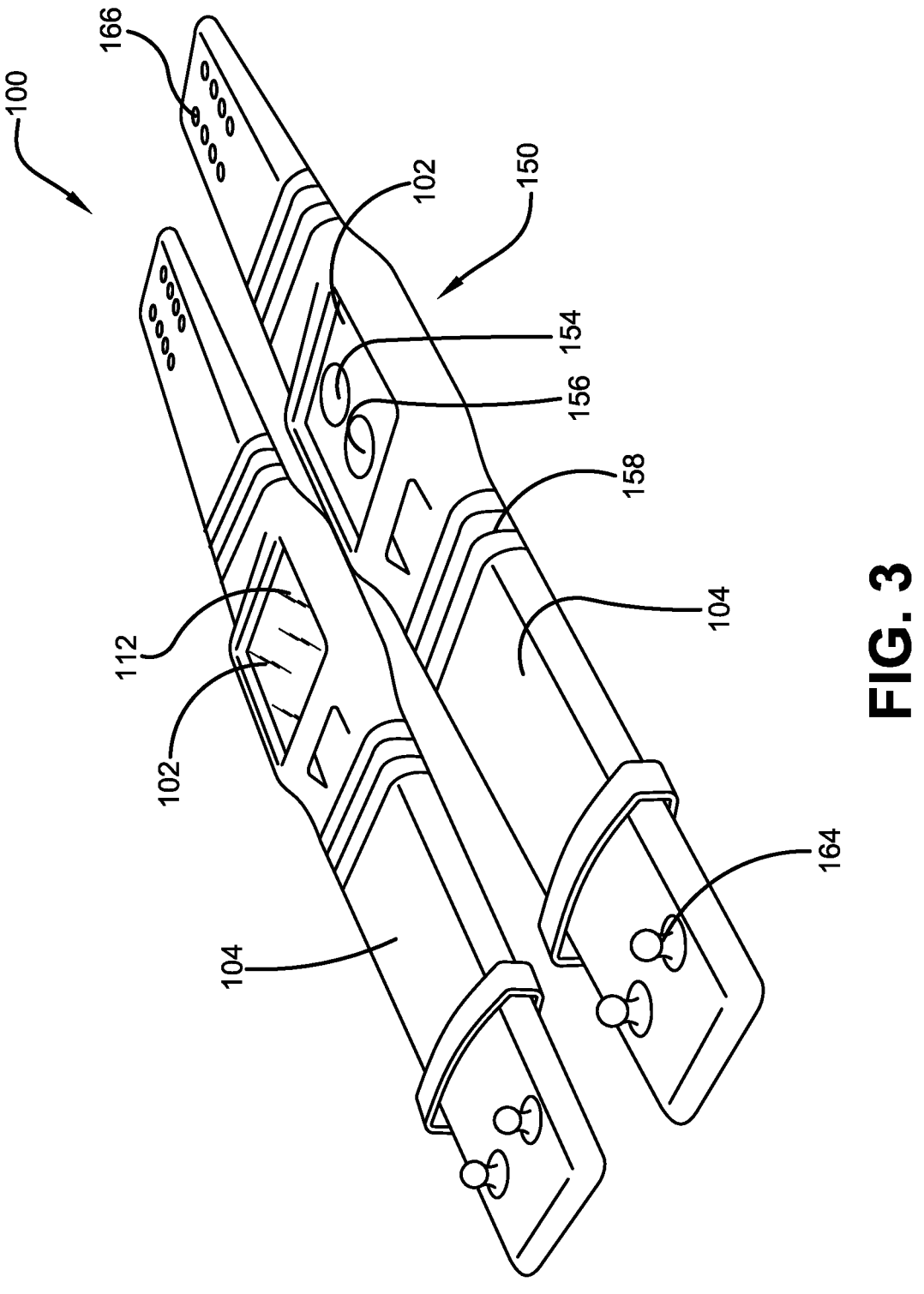
FIG. 3 illustrates a front perspective view of one embodiment of the vital sign monitoring device of the present invention showing the wristband components in accordance with the disclosed architecture.

Referring initially to the drawings, FIGS. 1-3 illustrate a perspective view of one embodiment of the vital sign monitoring device 100 of the present invention. In the present embodiment, the vital sign monitoring device 100 is a wearable vital sign monitoring device 100 that monitors a user's cardiovascular and pulmonary conditions. Specifically, the vital sign monitoring device 100 comprises a base component 102 with a plurality of monitors 106 that is secured within a wristband component 104 for use. The device 100 records vital signs of the user and triggers alarms when vital signs exceed specific parameters.

Generally, the vital sign monitoring device 100 is an extremely compact and lightweight, full function cardiac and pulmonary monitor that conveniently and comfortably can be worn on the wrist of a user, because the form factor and size of the monitor's housing (i.e., base component 102) relative to the conventional wristband is only slightly larger than a traditional digital watch.

Furthermore, the vital sign monitoring device 100 is configured to be worn by a user on a wrist 110 or forearm 108. Thus, a user can wear the vital sign monitoring device 100 while performing activities. Such activities include both vigorous activities and sedentary activities. A few examples include running, bicycling, swimming, climbing, skiing, weightlifting, boxing, martial arts, gardening, desk work, resting, sleeping, etc., or any other suitable activity as is known in the art.

Figure 4:
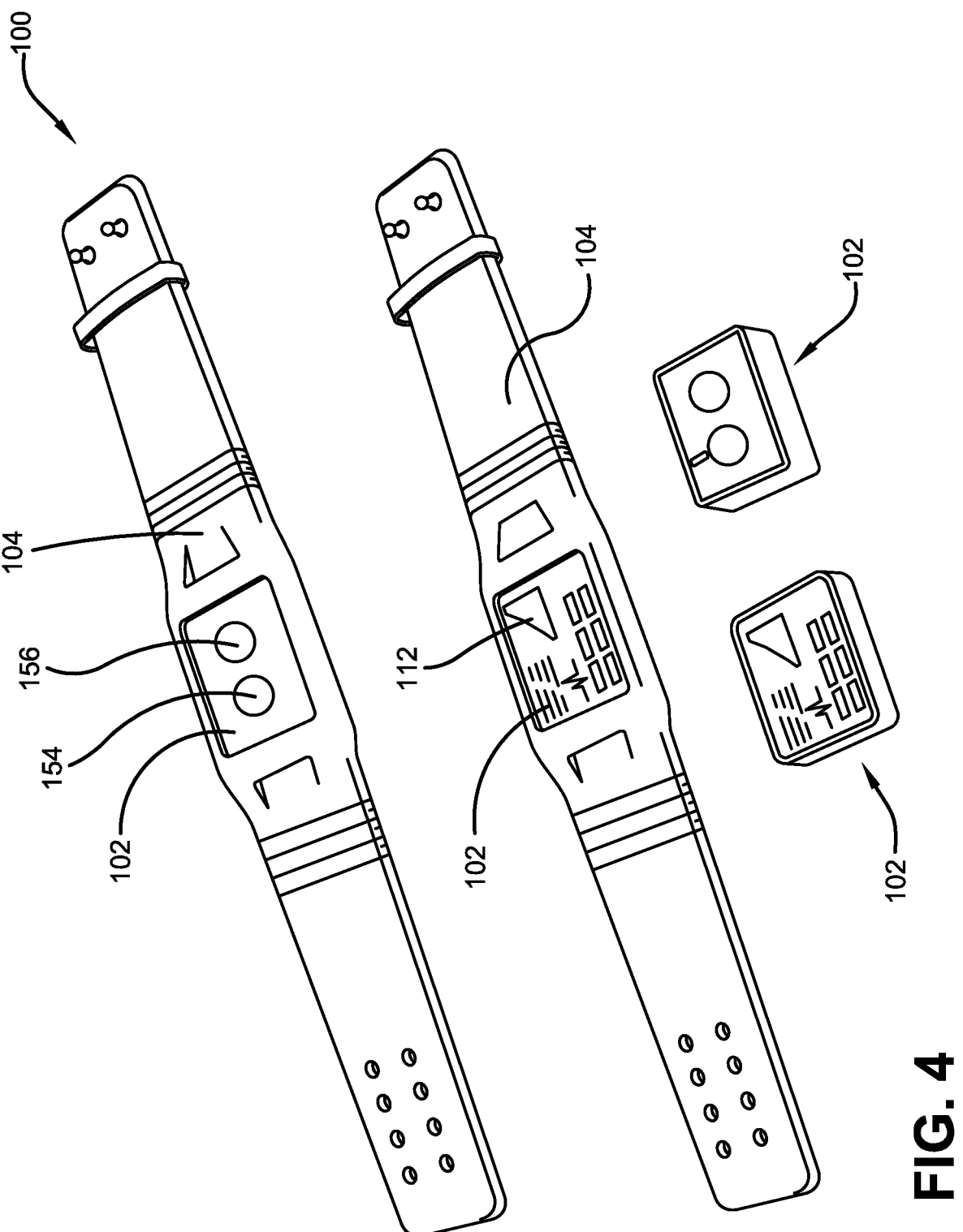
FIG. 4 illustrates a front perspective view of one embodiment of the vital sign monitoring device of the present invention showing the base components in accordance with the disclosed architecture.
Figure 5:
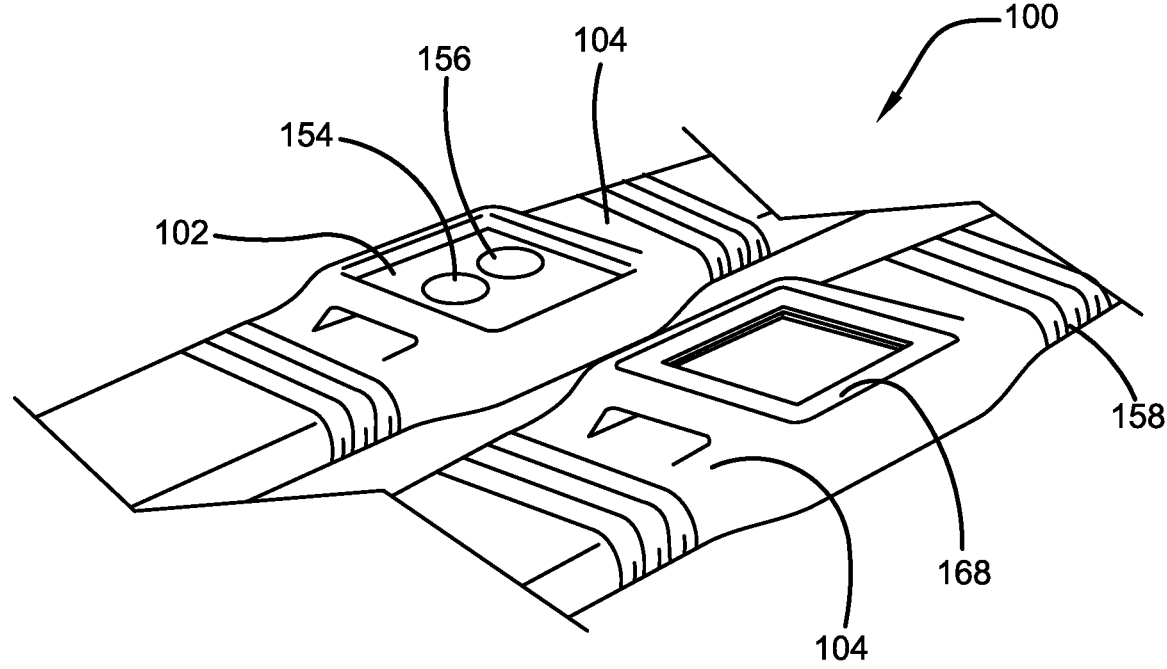
FIG. 5 illustrates a front perspective view of one embodiment of the vital sign monitoring device of the present invention showing the base component removed from the wristband component in accordance with the disclosed architecture.
Figure 6:
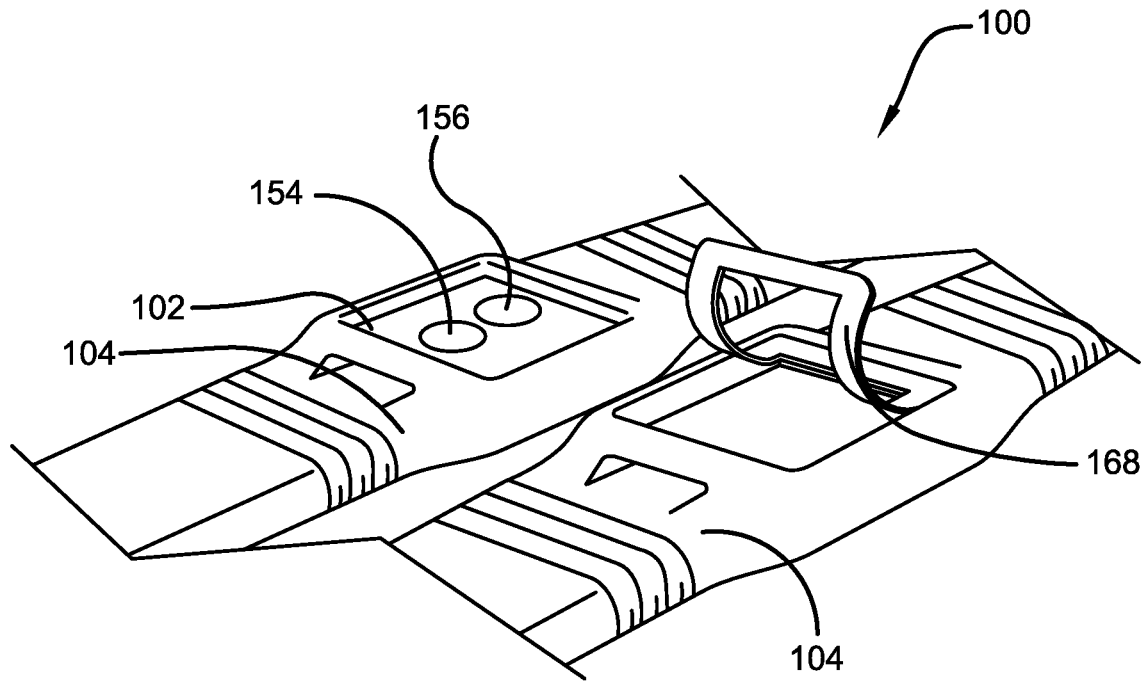
FIG. 6 illustrates a front perspective view of one embodiment of the vital sign monitoring device of the present invention showing how the base component is inserted into the wristband component in accordance with the disclosed architecture.

As shown in FIGS. 4-6, the vital sign monitoring device 100 comprises a base component 102 that can be any suitable shape and size as is known in the art, as long as the base component 102 is not much bigger than a traditional watch or smartwatch so that it can be worn comfortably by a user. Further, the base component 102 must be large enough to house a plurality of vital sign monitors 106 and data generation means. Generally, the base component 102 is rectangular in shape, but can be circular, square, oval, etc., or any other suitable shape as is known in the art. In some embodiments, the base component 102 can be made of varying sizes, such that smaller sizes would be used for a woman and larger sizes used for a man.

In one embodiment, the base component 102 comprises a touchscreen 112 that allows a user to enable and program the device 100 via touching points on the screen 112. In another embodiment, the base component 102 comprises functional buttons 114 to enable a user to program and utilize the device 100. In yet another embodiment, the base component 102 comprises both a touchscreen 112 and functional buttons 114 to enable a user to program the device 100.

Furthermore, the base component 102 comprises a plurality of vital sign monitors 106. Vital sign monitors 106 include a blood pressure monitor 116, a pulse monitor 118, an oximeter 120, an EKG lead 122, a respiration monitor 124, etc., or any other suitable monitor 106 as is known in the art. The plurality of vital sign monitors 106 measure the pulse, blood pressure, tissue oximetry, respiratory rate, EKG lead of a user, etc., or any other suitable vital statistics as is known in the art. Further, the base component 102 comprises electrodes 126, sensors 128, etc., and any other electronics 130 needed to measure the plurality of vital signs.

Additionally, the base component 102 comprises a plurality of electronics 130 for measuring and monitoring vital signs, as well as recording data. The electronics 130 can include, but are not limited to, an EKG signal amplifier and hardware filters coupled with electrodes 126 for producing an analog signal representative of the electrical field on the surface of a user's skin and between the electrodes 126 to measure a user's EKG lead. Electronics 130 also include analog-to-digital signal conversion means (or analog-to-digital converter (ADC)), and an amplifier for producing digital data representing the user's EKG waveform over a predefined interval of time. Further, electronics 130 preferably include static read-and-write memory (SRAM) that operates as a means for recording digital data produced by the ADC. Additional electronics 130 include a microcontroller with read-only memory (ROM), a digital-to-analog converter (DAC), a voltage-controlled oscillator (VCO), and a speaker 132 for wirelessly, and preferably audibly, communicating data recorded in the SRAM to a remote site for verification, real-time diagnosis, and/or archival recording.

In one embodiment, the vital sign monitoring device 100 measures a user's blood pressure. In contrast to a traditional blood pressure cuff, blood pressure may instead be measured by actuating an artery against a pressure sensor; for instance, by pushing the side of the index finger (where the radial artery resides) or the wrist 110 against a force sensor 134 whilst a photoplethysmogram or other blood flow pulse sensor 136 measures the volume of blood passing through the artery. The user may be instructed on how much force to apply with his finger or wrist 110 by providing visual or audio feedback with the readings from the force sensor 134. In this manner, signals corresponding to those of a traditional blood pressure cuff are captured, a varying and known force/pressure against an artery and a measure of the heartbeat signal (via i.e., EKG) to that force/pressure. The shape of the force sensor 134 may be shaped in such a way as to accept the finger so that the relationship of force to pressure is well understood (i.e., linear). Further, a blood pulse amplitude sensor located on the back of the user's wrist 110 may obtain blood pulse amplitude data from a capillary bed on the back of the user's wrist 110, while a blood pulse amplitude sensor located on the front of the user's wrist (palm side) may obtain blood pulse amplitude data from a radial artery on the user's wrist 110.

Systolic and or diastolic blood pressure readings can be obtained by measuring variations in the amplitude of pulses in blood vessels such as pulses in the volume of blood through arteries or capillary beds. Variations in blood pulse amplitude can be induced by applying varying external pressure against the blood vessels. In conventional oscillometric techniques for measuring blood pressure, an inflatable cuff applies the varying external pressure. In various embodiments of this disclosure, a user manually pushes against a location on his or her body and thereby applies the varying external pressure on the underlying blood vessels. And while the user manually applies variable pressure, a sensor measures the blood pulse amplitude. A measuring device estimates the user's blood pressure from the pulse amplitude as a function of externally applied pressure.

In various embodiments, the blood pulse amplitude is determined using an optical sensor, such as a PPG sensor 136, which measures variations in blood volume through arteries. By measuring variations in amplitude of the PPG signal (and hence variations in blood volume amplitude pulses) as a function of variations in external pressure applied to the blood vessels used to generate PPG signal, sufficient information can be acquired to determine the systolic and/or diastolic blood pressure of a user.

In accordance with various embodiments, a user applies a variable pressure to his or her blood vessels while a PPG sensor 136 measures the amplitude of blood volume pulses. The resulting PPG signal and associated pressure data is used to calculate blood pressure. Standard approaches to determining blood pressure from oscillometric data can be used.

In certain implementations, the blood pulse amplitude sensor is a photoplethysmogram (PPG) sensor 136 including a light emitter and a light detector configured to generate PPG sensor data, but not limited to. Many other pressure sensitive techniques for measuring blood pulse amplitude may be used to estimate blood pressure in accordance with embodiments of this disclosure. In certain implementations, the blood pulse amplitude sensor is a bioelectrical imped-ance analysis (BIA) sensor or a ballistocardiograph (BCG) sensor.

In some embodiments, one or more processors 138 are incorporated in the base component 102 with the sensors 128. In certain embodiments, the vital sign monitoring device 100 includes a wireless transmitter 140 configured to transmit the blood pulse amplitude data and the variable force and/or pressure data to a remote device 142. Further, at least one of the one or more processors 138 may be located in the remote device 142. Specifically, the device 100 additionally includes a wireless transmitter 140 config-ured to transmit blood pulse amplitude data and variable force and/or pressure data to a remote device 142. The transmitter 140 may be attached to or contained in the base component 102. In certain embodiments, the one or more processors 138 are located in the remote device 142. The remote device 142 may be, for example, a smart phone, a tablet, a personal computer (i.e., a laptop computer), a server, a distributed computing environment, etc.

The one or more processors 138 are typically integrated circuits, which may be general purpose integrated circuits or custom designed (or optimized) integrated circuits, such as digital signal processors. The processor(s) 138 may operate under the control of program instructions including, for example, machine code and/or microcode stored on memory available to the processor(s) or embedded in the processor as, for example, firmware. As examples, the memory includes volatile memory such as random-access memory (DRAM or SRAM) or non-volatile memory such as read only memory (ROM), EPROM, flash memory, and the like. Some or all of the memory may be disposed on the same integrated circuit that executes the instructions. Thus, in some embodiments, some or all of the memory may be considered to be included in the processor(s) 138.

In certain embodiments, the vital sign monitoring device 100 tracks the user's activity and uses activity type and/or activity level in determining whether to estimate blood pressure or how to estimate blood pressure. For example, the device 100 may detect that a user just completed an exercise and based on that, the device 100 may determine that is should not take a blood pressure reading or use a more stringent algorithm blood pressure estimation. This approach may be appropriate when the activity type or activity level is known to produce a blood pressure reading that would likely be inaccurate.

In one embodiment, the vital sign monitoring device 100 comprises a means for recording data received from the monitoring of vital signs. This data can be graphically displayed to a user via the touchscreen 112 of the base component 102. For example, users can read and record their measurements on the left side 144 of the screen 112. If the user wishes to view a detailed readout of one of their measurements, the user merely touches the measurement on the left side 144 of the screen 112. Once the measurement is selected by the user, the detailed analysis appears on the right side 146 of the screen 112. Further, any other suitable user interface can be utilized to display the measurements, as is known in the art. Vital sign measurements are recorded as the device 100 is used. Further, the data can be transferred remotely via a wireless connection. Thus, the data can be monitored and recorded remotely in real-time, as well. Base parameters for vital sign measurements can be established and set with the device 100, such that if a user's measure-ments are outside of the base parameters, an alarm is sounded. Specifically, if one of a user's measurements moves into a red zone (i.e., outside of the set base param-eters), the right side 146 of the screen 112 will automatically display the dangerous measurement. At such a point, an alarm will begin to notify a user of the situation. The alarm can be audible and/or visual. For example, the base com-ponent 102 can comprise speakers 132 to sound an alarm when a measurement enters the red zone. Further, the base component 102 can comprise lights 148 to flash an alarm when a measurement enters the red zone. In one embodi-ment, the base component 102 comprises lights 148 and speakers 132 to sound and flash an alarm when a measure-ment enters the red zone.

Additionally, the vital sign monitoring device 100 com-prises a second device 150 wherein the base component 102 comprises the same size and shape as the previous base component 102 and contains the same electronics 130 and vital sign monitors 106. However, the second device 150 does not comprise a touchscreen 112 showing vital sign measurements but contains a hard plastic surface 152 with at least two tactile buttons 154 and 156. The first button 154 syncs its Bluetooth to the first base component 102. Further, the second device 150 also comprises an LED light 156 next to the syncing button 154 that illuminates green once the Bluetooth is synced. Any suitable number of buttons can be utilized as is known in the art.

In use, the two base components 102 are each secured within a wristband component 104 and worn on a user's wrist 110 or forearm 108. Once synced and functioning, the device 100 continuously measures pulse, blood pressure, tissue oximetry, respiratory rate, and an EKG lead. In one embodiment, only a single wristband device 104 is used. If only one device 100 is used, the respiratory rate and EKG cannot be monitored, but other vital signs can be measured. With the use of both devices 100 and 150, pulse, blood pressure, tissue oximetry, respiratory rate, and an EKG lead can all be measured accurately.

Figure 7:
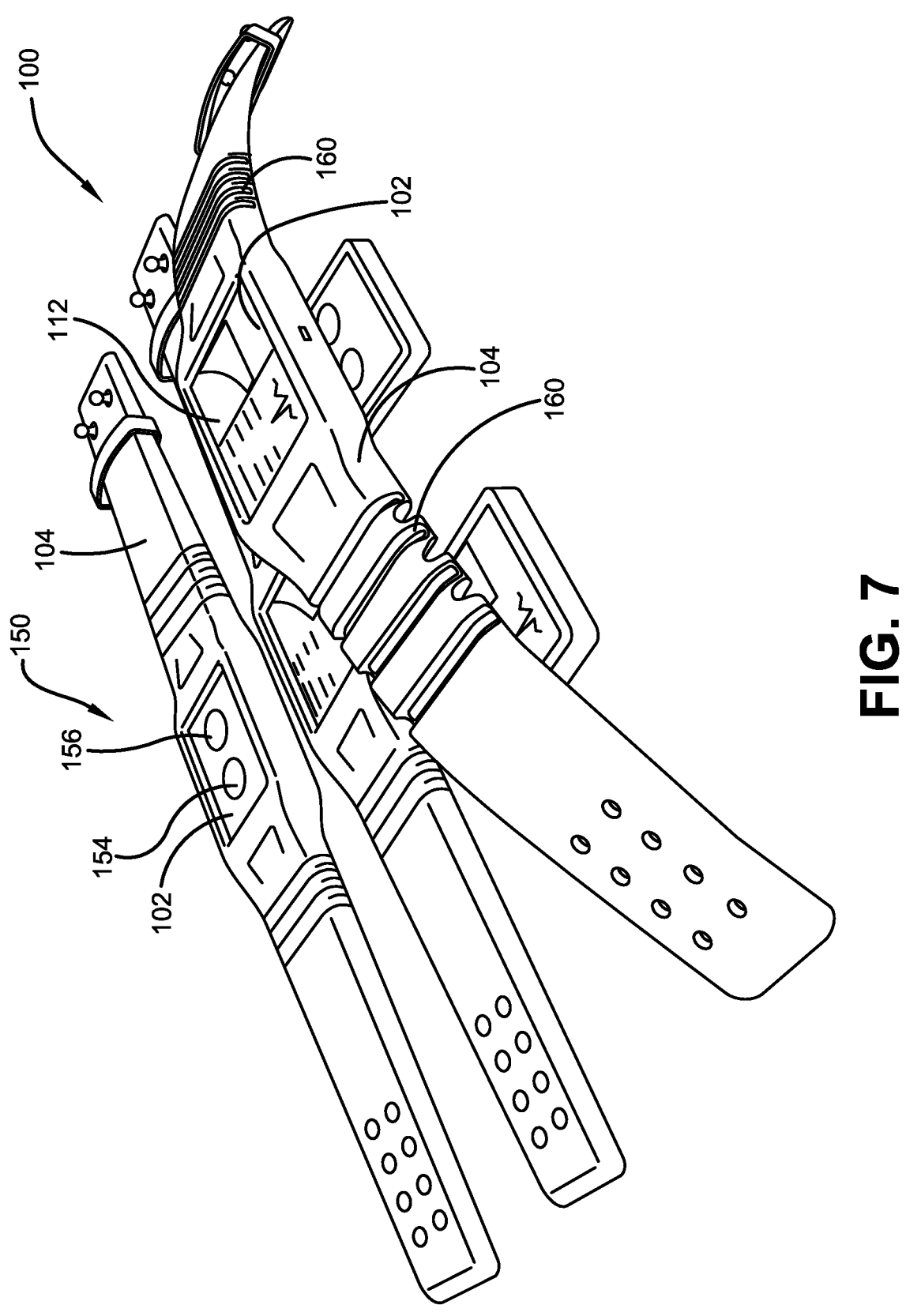
FIG. 7 illustrates a front perspective view of one embodiment of the vital sign monitoring device of the present invention showing the tension warning component in accordance with the disclosed architecture.
Figure 8:
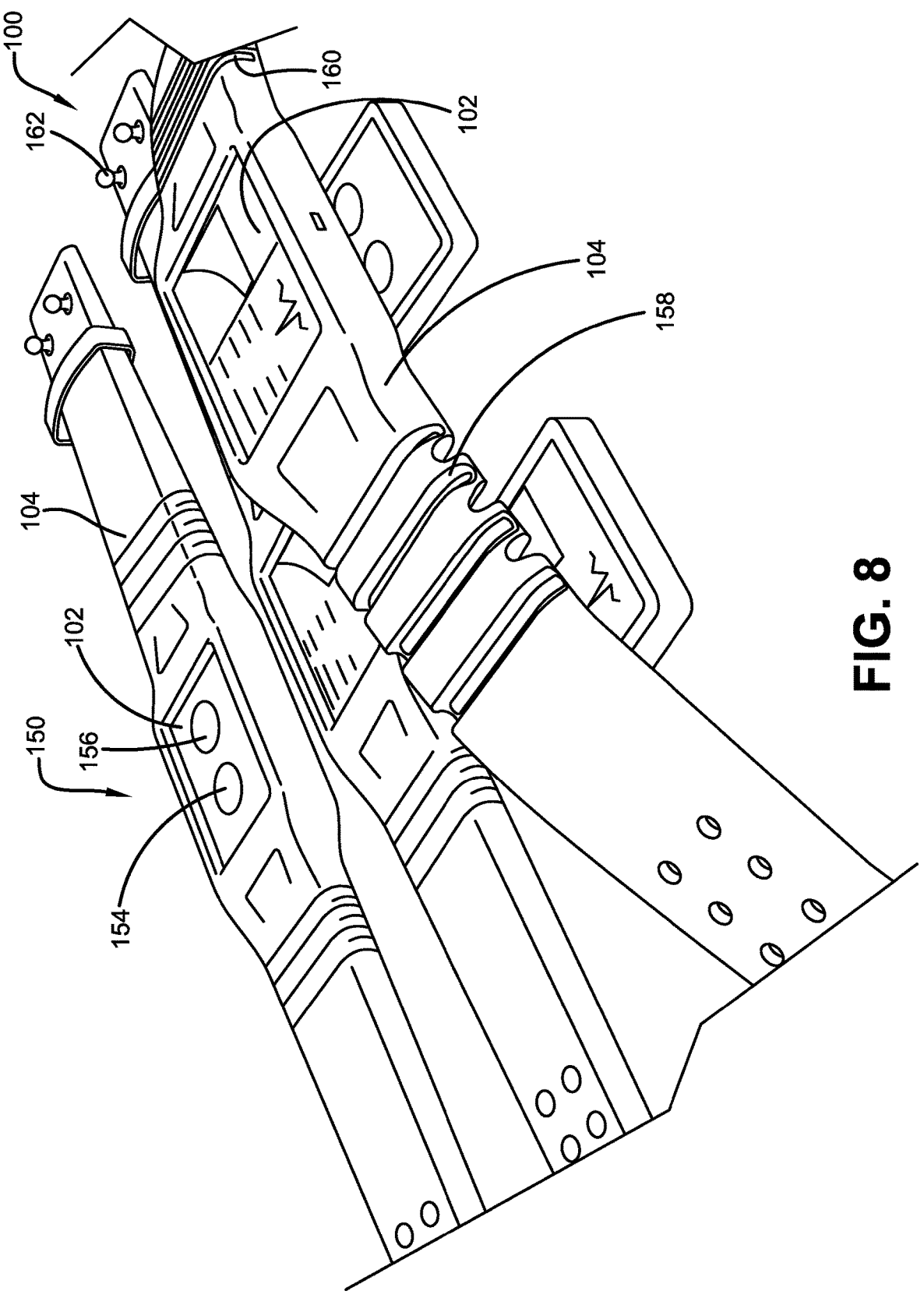
FIG. 8 illustrates a front perspective view of one embodiment of the vital sign monitoring device of the present invention showing the grooves of the wristband component in accordance with the disclosed architecture.
Figure 9:
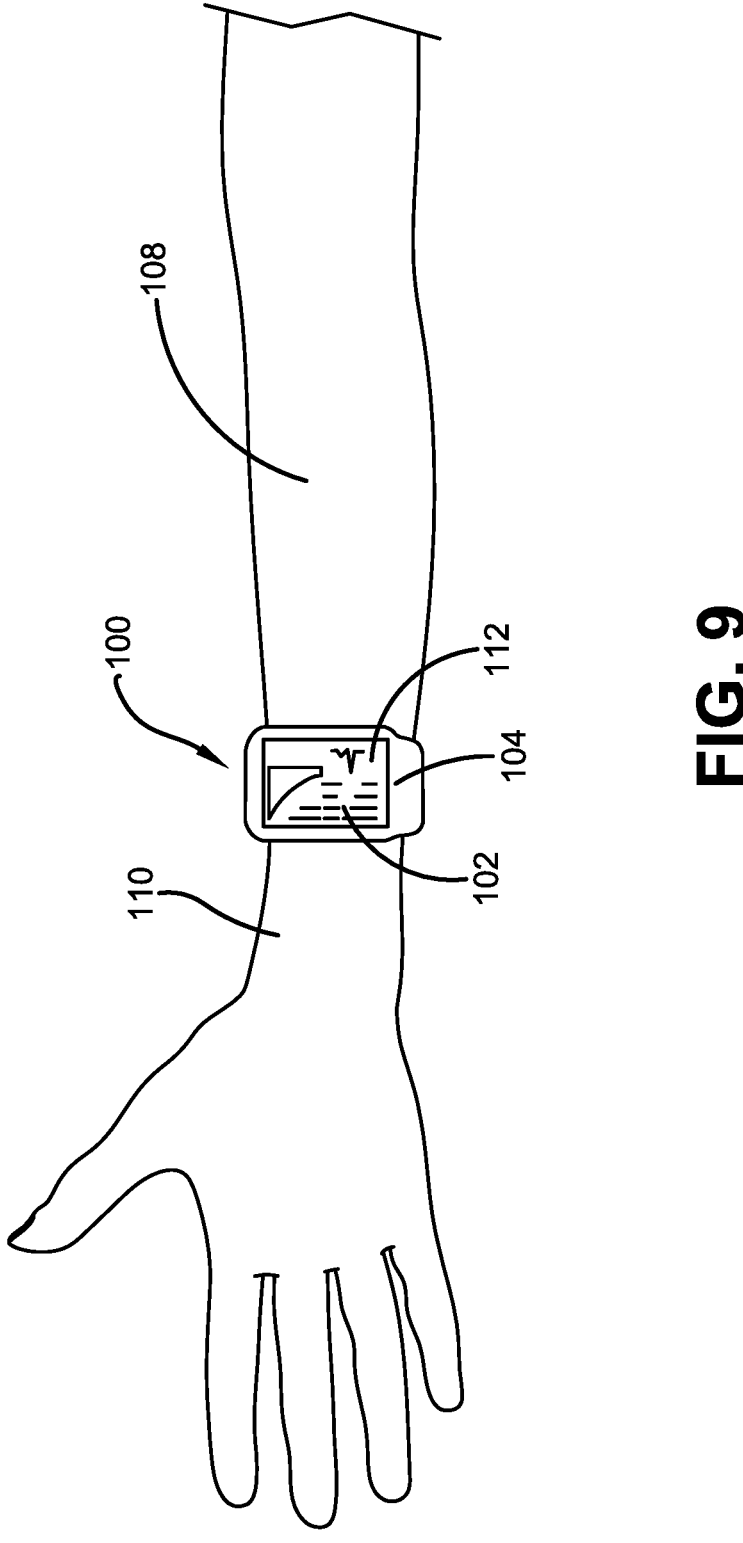
FIG. 9 illustrates a front perspective view of one embodiment of the vital sign monitoring device of the present invention showing the device in use in accordance with the disclosed architecture.

As shown in FIGS. 7-9, the wristband component 104 is a conventional watchband of any suitable size and structure and, entirely contains the base component 102, electronics 130, sensors 128, etc. While the term wrist "band" is used herein, it is intended to cover all types of structure for fixing the base component 102 to the user's wrist 110. The band may have a wide range of rigidities, so long as it can conform generally to the shape of the user's wrist 110. The concept of a wristband includes flexible wrist straps and bracelets with links. It also includes fixing structures that attach to watch faces and the like.

Further, the wristband component 104 comprises a ten-sion warning which alerts a user when the band is worn too tightly. Specifically, the wristband component 104 comprises corrugated sides 158 on the band. Warnings 160 are printed within the folds of the corrugated sides 158, such that the warnings 160 are not displayed when the band is not stretched. If the band becomes stretched, the corrugated sides 158 expand and open displaying the warnings 160 to reduce tension on the band.

In one embodiment, the wristband component 104 comprises a latch 162 with inserts or prongs 164 that fit into two to four holes 166, depending on the wants and/or needs of a user. Further, the wristband component 104 comprises a flap or frame segment 168 that lifts up and away from the band to allow the base component 102 to be inserted into the screen face opening of the band. Once positioned in the band, the flap 168 is secured back down to secure the base component 102 within the band. The flap 168 can have a notch, a tab, a lock, a pressure-fit, etc., to secure the flap 168 in place once the base component 102 has been inserted.

Figure 10:
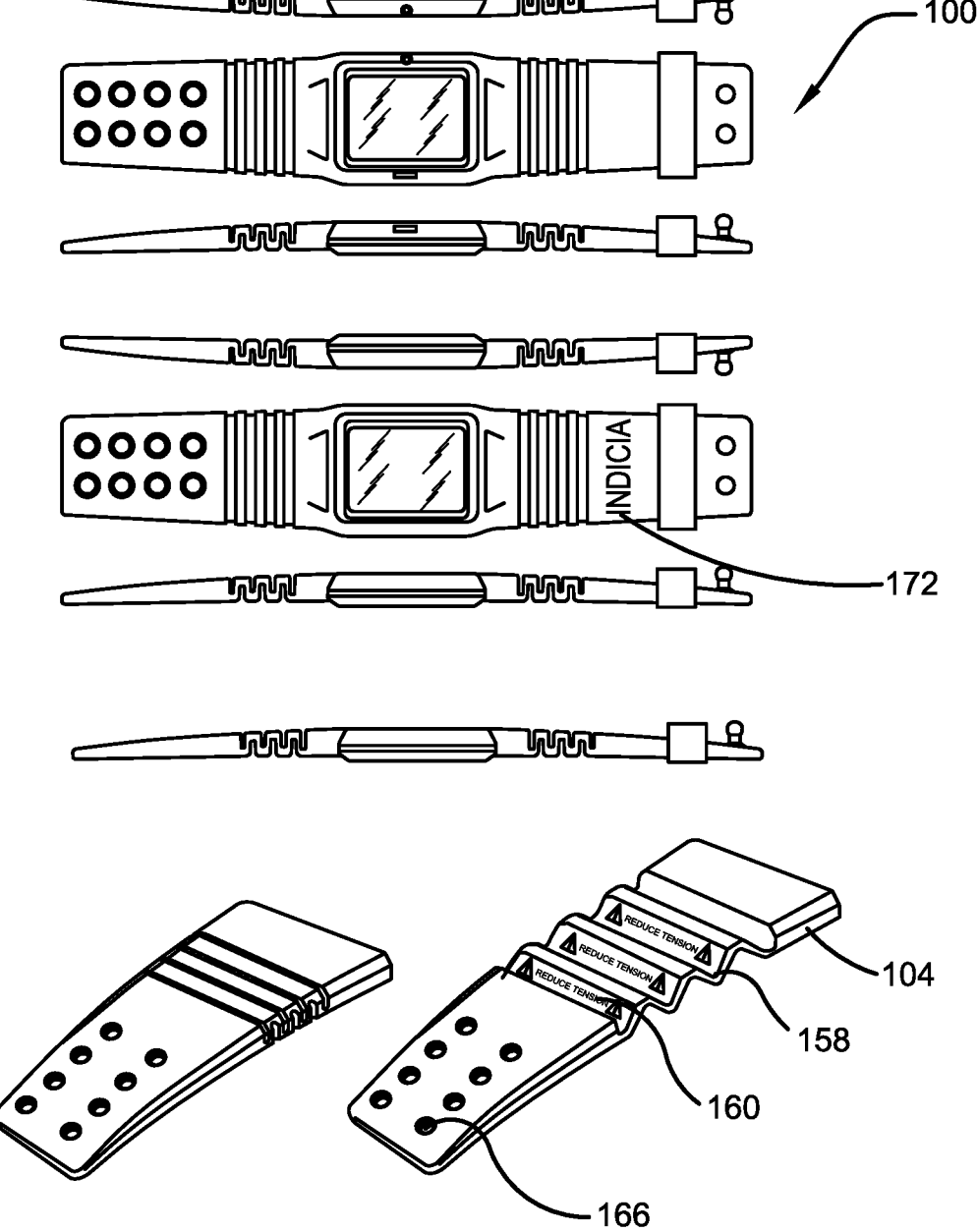
FIG. 10 illustrates a front perspective view of one embodiment of the vital sign monitoring device of the present invention showing the schematics of the device in accordance with the disclosed architecture.
Figure 11:
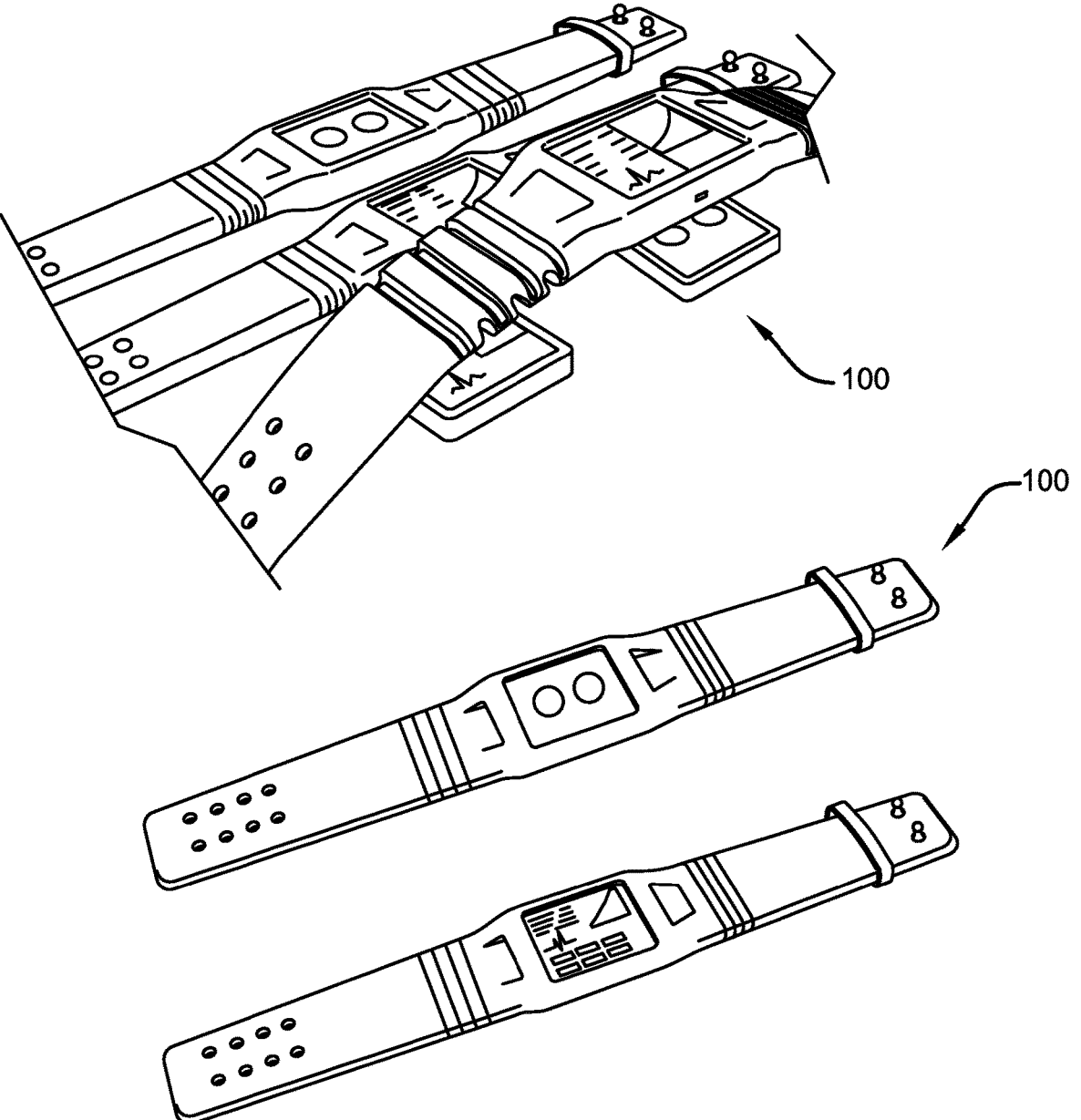
FIG. 11 illustrates a front perspective view of one embodiment of the vital sign monitoring device of the present invention in accordance with the disclosed architecture.

As shown in FIGS. 10-11, the device 100 comprises a speaker 132, lights 148, a micro-USB port 170, etc., or any other suitable components as is known in the art, depending on the needs and/or wants of a user.

Furthermore, the device 100 is water resistant/waterproof or manufactured with a coating that is water resistant/waterproof.

Those skilled in the arts will appreciate that the illustrated and described base component 102, particularly of the electrodes 126, sensors 128, and electronics 130, achieve the extremely high functionality described herein, however, it is possible that alternative device selection and circuit topology, electronics, sensors, and/or electrodes might be used within the spirit of the invention. Those of skill also will appreciate that in accordance with the preferred embodiment, the base component 102 and/or wristband component 104 are molded plastic, such as acrylonitrile-butadiene-styrene (ABS), which renders the device 100 extremely rigid and durable, but also lightweight and relatively inexpensive to manufacture.

In yet another embodiment, the vital sign monitoring device 100 comprises a plurality of indicia 172. The base component 102 of the device 100 may include advertising, trademark, other letters, designs, or characters, printed, painted, stamped, or integrated into the base component 102, or any other indicia 172 as is known in the art. Specifically, any suitable indicia 172 as is known in the art can be included, such as, but not limited to, patterns, logos, emblems, images, symbols, designs, letters, words, characters, animals, advertisements, brands, etc., that may or may not be watch, vital sign, or brand related.

FIG. 12 illustrates a flowchart of the method of monitoring a user's cardiovascular and pulmonary conditions via a wearable monitor. The method includes the steps of at 1200, providing a vital sign monitoring device comprising a base component with a blood pressure monitor, a pulse monitor, an oximeter, an EKG lead, and a respiration monitor. The method also comprises at 1202, securing the base component inside a wristband component for use. Further, the method comprises at 1204, securing the wristband component to a user's wrist. The method also comprises at 1206, securing a second coordinating wristband component to a user's other wrist. The method comprises at 1208, turning on the device and linking the Bluetooth to connect both devices. Finally, the method comprises at 1210, monitoring a user's cardiovascular and pulmonary conditions via the wearable monitors.

The vital sign monitoring device 100 provides for the remote monitoring of the vital alert parameters beyond the local wrist band wearer, which has great importance for oversight purposes and as the technical extension of the worn monitors. Further, the vital sign monitoring device 100 has wide applicability beyond police work, and may also be used in a medical facility, emergency room, operating room, recovery room, ICU, stepdown, as well post discharge.

Certain terms are used throughout the following description and claims to refer to particular features or components. As one skilled in the art will appreciate, different users may refer to the same feature or component by different names. This document does not intend to distinguish between components or features that differ in name but not structure or function. As used herein "vital sign monitoring device", "monitoring device", and "device" are interchangeable and refer to the vital sign monitoring device 100 of the present invention.

Notwithstanding the foregoing, the vital sign monitoring device 100 of the present invention can be of any suitable size and configuration as is known in the art without affecting the overall concept of the invention, provided that it accomplishes the above-stated objectives. One of ordinary skill in the art will appreciate that the vital sign monitoring device 100 as shown in FIGS. 1-12 are for illustrative purposes only, and that many other sizes and shapes of the vital sign monitoring device 100 are well within the scope of the present disclosure. Although the dimensions of the vital sign monitoring device 100 are important design parameters for user convenience, the vital sign monitoring device 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A vital sign monitoring device that is a wearable monitor for monitoring a user's vital signs, the vital sign monitoring device comprising:

a base component;

a plurality of vital sign sensors; and a wristband component configured to be worn on a user's wrist;

a second device with a base component that syncs to the vital sign monitoring device to provide more accurate measuring of vital signs;

wherein the base component is secured within the wristband component for use;

wherein the user can wear the vital sign monitoring device while performing activities;

wherein the base component houses the plurality of vital sign sensors;

wherein the base component comprises a touchscreen;

wherein the plurality of vital sign sensors comprise a blood pressure monitor, a pulse monitor, an oximeter, an EKG lead, and a respiration monitor;

wherein the plurality of vital sign sensors measure pulse, blood pressure, tissue oximetry, and respiratory rate of a user;

wherein the base component comprises a plurality of electronics which include an EKG signal amplifier, hardware filters coupled with electrodes for producing an analog signal representative of an electrical field on a surface of a user's skin and between the electrodes to measure a user's EKG lead;

wherein the base component comprises a force sensor and a PPG sensor for measuring a user's blood pressure;

wherein the wristband component comprises a tension warning which alerts a user when the band is worn too tightly;

wherein the tension warning comprises corrugated sides which unfold to display warnings when the wristband component is stretched too tight on a user's wrist; and further wherein the plurality of vital sign sensors record vital signs of a user and trigger alarms when the vital signs exceed specific parameters.

2. The vital sign monitoring device of claim 1, wherein the wristband component comprises a flap that lifts up and away from the wristband component to allow the base component to be inserted and secured.

3. The vital sign monitoring device of claim 2, wherein the base component is water resistant or waterproof, or manufactured with a coating that is water resistant or waterproof.

4. The vital sign monitoring device of claim 3 further comprising a plurality of indicia.

* * * * *